United States Patent [19]

Fick

[11] Patent Number: 6,096,303
[45] Date of Patent: Aug. 1, 2000

[54] METHOD TO ENHANCE TREATMENT OF CYSTIC TUMORS

[75] Inventor: James R. Fick, Martinez, Ga.

[73] Assignee: Medical College of Georgia Research Institute, Inc., Augusta, Ga.

[21] Appl. No.: 08/904,097

[22] Filed: Jul. 31, 1997

[51] Int. Cl.$^7$ .......................... A61K 48/00; C12N 15/63
[52] U.S. Cl. ..................... 424/93.2; 424/93.21; 435/455; 435/456
[58] Field of Search .................................. 424/93.1, 93.2, 424/93.21; 435/325, 366, 455, 456

[56] References Cited

U.S. PATENT DOCUMENTS

| | | | |
|---|---|---|---|
| 4,352,883 | 10/1982 | Lim | 435/178 |
| 4,868,116 | 9/1989 | Morgan et al. | 435/456 |
| 4,980,286 | 12/1990 | Morgan et al. | 435/69.1 |
| 5,558,852 | 9/1996 | Bigner et al. | 424/1.49 |

FOREIGN PATENT DOCUMENTS

| | | |
|---|---|---|
| WO 89/07136 A2 | 8/1989 | WIPO . |
| WO 90/02806 A1 | 3/1990 | WIPO . |
| WO 93/17669 A1 | 9/1993 | WIPO . |
| WO 94/25080 A1 | 11/1994 | WIPO . |
| WO 96/20732 | 7/1996 | WIPO . |
| WO 96/21470 | 7/1996 | WIPO . |
| WO 97/28179 | 8/1997 | WIPO . |

OTHER PUBLICATIONS

Gura (Nov. 1997) Systems for identifying new drugs are often faulty. Science 278:1041–1042.
Verma et al. Gene therapy—promises, problems and prospects. Nature 389:239–242, Sep. 1997.
Alkan–Onyuksel, et al., "A Mised Micellar Formulation Suitable for the Parenteral Administration of Taxol," *Pharm. Res.* 11(2):206–212 (1994).
Bagshawe, et al., "A cytotoxic agent can be generated selectively at cancer sites," *Br. J. Cancer* 58:700–703 (1988).
Bagshawe, "The First Bagshawe Lecture Towards generating cytotoxic agents at cancer cites," *Br. J. Cancer* 60:275–281 (1989).
Balzarini, et al., "Differential Mechanism of Cytostatic Effect of (E)–5–(2–Bromovinyl)–2'–deoxyuridine, 9–(1, 3–Dihydroxy–2–propoxymethyl)guanine, and Other Antiherpetic Drugs on Tumor Cells Transfected by the Thymidine Kinase Gene of Herpes Simplex Virus Type 1 or Type 2," *J. Biol. Chem.* 268(9):6332–6337 (1993).
Banerji, et al., "A Lymphocyte–Specific Cellular Enhancer is Located Downstream of the Joining Region in Immunoglobulin Heavy Chain Genes," *Cell* 33(3):729–740 (1983).
Battelli, et al., "T lymphocyte killing by a xanthine–oxidase–containing immunotoxin," *Cancer Immunol. Immunother.* 35(6):421–425 (1992).

Berkner, et al., "Abundant Expression of Polyomavirus Middle T Antigen and Dihydrofolate Reductase in an Adenovirus Recombinant," *J. Virology* 61(4):1213–1220 (1987).
Bout, "Lung Gene Therapy: In Vivo Adenovirus–Mediated Gene Transfer to Rhesus Monkey Airway Epithelium," *Human Gene Therapy* 5(1):3–10 (1994).
Braunwald, et al., eds., "Principals of Cancer Therapy," in *Harrison's Principles of Internal Medicine*, Eleventh Edition, Chapter 79 pp. 431–446, (McGraw–Hill Book Co., 1987).
Brem, et al., "Interstitial chemotherapy with drug polymer implants for the treatment of recurrent gliomas," *J. Neurosurg.* 74(3):441–446 (1991).
Brem, et al., "Polymers as Controlled Drug Delivery Devices for the Treatment of Malignant Brain Tumors," *Eur. J. Pharm. Biopharm.* 39(1):2–7 (1993).
Brem, et al., "Intraoperative Chemotherapy Using Biodegradable Polymers: Safety and Effectiveness for Recurrent Glioma Evaluated by a Prospective, Multi–Institutional, Placebo–Controlled Clinical Trial," *Proc. Amer. Clin. Oncology*, p. 174, Abstract No. 487, (1994).
Brown, et al., "Review Article—Molecular and Cellular Mechanisms of Receptor–Mediated Endocytosis," *DNA and Cell Biology* 10(6):399–409 (1991).
Brown, et al., "Penetration of Host Cell Membranes by Adenovirus 2," *J. Virology* 12(2):386–396 (1973).
Bruce, et al., "Comparson of the Sensitivity of Hematopoietic Colony–Forming Cells in Different Proliferative States of 5–Fluorouracil," *J. Natl. Cancer Inst.* 38(3):401–405 (1967).
Caillaud, "Adenoviral Vector as a Gene Delivery System into Cultured Rat Neuronal and Glial Cells," *Eur. J. Neuroscience* 5(10):1287–1291 (1993).

(List continued on next page.)

*Primary Examiner*—Robert A. Schwartzman
*Attorney, Agent, or Firm*—Arnall Golden & Gregory, LLP

[57] ABSTRACT

It has been discovered that cells such as genetically engineered fibroblasts and keratinocytes can be cultured in the cyst fluid of encapsulated tumors. This provides a means for proliferating genetically engineered producer cells within these types of tumors, increasing the number of cells producing viral particles, which then transduce the surrounding tumor cells with the genetic material, in the preferred embodiment, a lethal gene. A number of different tumor types form "cysts", which contain fluid produced by the tumor cells, including brain tumor cells such as gliomas, and many types of breast, and lung tumors. These cyst fluids have been shown to contain elevated levels of certain growth factors, for example, fibroblast growth factor (FGF) and epidermal growth factor (EGF). The types of genetically engineered cells to be used can be selected in part according to the levels of growth factors in the cyst fluid which most promote growth of the cells, for example, cystic tumors with high levels of FGF would be injected with genetically engineered fibroblasts; cystic tumors with high levels of EGF would be injected with genetically engineered keratinocytes; and cystic tumors with high levels of vascular endothelial growth factor (VEGF) would be injected with genetically engineered endothelial cells.

22 Claims, 2 Drawing Sheets

OTHER PUBLICATIONS

Chardonnet, et al., "Early Events in the Interaction of Adenoviruses with HeLa Cells," *Virology* 40(3):462–477 (1970).

Culver, et al., "In Vivo Gene Transfer with Retroviral Vector–Producer Cells for Treatment of Experimental Brain Tumors," *Science* 256:1550–1552 (1992).

Davidson, et al., "Overproduction of Polyomavirus Middle T Antigen in Mammalian Cells through the Use of an Adenovirus Vector," *J. Virology* 61(4):1226–1239 (1987).

Fiers, et al., "Complete nucleotide sequence of SV40 DNA," *Nature* 273(5657):113–120 (1978).

Frattini, et al., "In Vitro synthesis of oncogenic human papillomaviruses requires episomal genomes for differentiation–dependent late expression," *Proc. Natl. Acad. Sci. USA* 93:3062–3067 (1996).

* Friedmann, "Overcoming the obstacles to gene therapy," *Scientific American* Jun.:96–101 (1997).

Gomez–Foix, "Adenovirus–mediated Transfer of the Muscle Glycogen Phosphorylase Gene into Hepatocytes Confers Altered Regulation of Glycogen Metabolism," *J. Biol. Chem.* 267(35):25129–25134 (1992).

Gottlieb, et al., "Treatment of Malignant Melanoma With Camptothecin (NSC–100880)," *Cancer Chemother. Rep.* 56(1):103–105 (1972).

Greenway, et al., "Human cytomegalovirus DNA: BamHl,–EcoRl and Pstl restriction–endonuclease cleavage maps," *Gene* 18:355–360 (1982).

Guzman, "Efficient Gene Transfer Into Myocardium by Direct Injection of Adenovirus Vectors," *Circulation Research* 73(6):1201–1207 (1993).

Haj–Ahmad, et al., "Development of a Helper–Independent Human Adenovirus Vector and Its Use in the Transfer of the Herpes Simplex Virus Thymidine Kinase Gene," *J. Virology* 57(1):267–274 (1986).

Hughes, et al., "Monoclonal Antibody Targeting of Liposomes to Mouse Lung in Vivo," *Cancer Research* 49(22):6214–6220 (1989).

Kirshenbaum, "Highly Efficient Gene Transfer into Adult Ventricular Myocytes by Recombinant Adenovirus," *J. Clin. Invest.* 92:381–387 (1993).

La Salle, "An Adenovirus Vector for Gene Transfer into Neurons and Glia in the Brain" *Science* 259:988–990 (1993).

Litzinger, et al., "Biodistribution and immunotargetability of ganglioside–stabilized dioleoylphosphatidylethanolamine liposomes," *Boichimica et Biophysica Acta* 1104(1):179–187 (1992).

Lusky, et al., "Bovine Papilloma Virus Contains an Activator of Gene Expression at the Distal End of the Early Transcription Unit," *Mol. Cell Bio.* 3(6):1108–1122 (1983).

Massie, et al., "Construction of a Helper–Free Recombinant Adenovirus That Expresses Polyomavirus Large T Antigen," *Mol. Cell. Biol.* 6(8):2872–2883 (1986).

Matsuda, et al., "Photoinduced Prevention of Tissue Adhesion," *ASAIO Trans.* 38(1):154–157 (1992).

Moertel, et al., "Phase II Study of Camptothecin (NSC–100880) in the Treatment of Advanced Gastrointestinal Cancer," *Cancer Chemother. Rep.* 56(1):95–101 (1972).

Morsy, "Efficient Adenoviral–mediated Ornithine Transcarbamylase Expression in Deficient Mouse and Human Hepatocytes," *J. Clin. Invest.* 92(3):1580–1586 (1993).

Moullier, "Correction of lysosmal storage in the liver and spleen of MPS VII mice by implantation of genetically modified skin fibroblasts," *Nature Genetics* 4(2):154–159 (1993).

Muggia, et al., "Phase I Clinical Trial of Weekly and Daily Treatment With Camptothecin (NSC–100880): Correlation With Preclinical Studies," *Cancer Chemother. Rep.* 56(4):515–521 (1972).

Mullen, et al., "Transfer of the bacterial gene for cytosine deaminase to mammalian cells confers lethal sensitivity to 5–fluorocytosine: A negative selection system," *Proc. Natl. Acad. Sci. USA* 89(1):33–37 (1992).

Mulligan, et al., "Expression of a Bacterial Gene in Mammalian Cells," *Science* 209(4463):1422–1427 (1980).

Mulligan, et al., "The Basic Science of Gene Therapy," *Science* 260:926–932 (1993).

* Oldfield, et al., "Gene therapy for the treatment of brain tumors using intra–tumoral transduction with the thymidine gene and intravenous ganciclovir," *Human Gene Therapy* 4:39–69 (1993).

Osborne, et al., "Transcription Control Region Within the Protein–Coding Portion of Adenovirus E1A Genes," *Mol. Cell Bio.* 4(7):1293–1305 (1984).

* Orkin, et al., "Report and recommendations of the panel to assess the NIH investment in research on gene therapy," (1995).

Pietersz, et al., "Antibody Conjugates for the Treatment of Cancer," *Immunolog. Reviews* 129:57–80 (1992).

Ragot, "Replication–defective recombinant adenovirus expressing the Epstein–Barr virus (EBV) envelope glycoprotein gp340/220 induces protective immunity against EBV–induced lymphomas in the cottontop tamarian," *J. Gen. Virology* 74(3):501–507 (1993).

Ram, et al., "In situ Retroviral–mediated Gene Transfer for the Treatment of Brain Tumors in Rats," *Cancer Res.* 53(1):83–88 (1993).

Rich, "Development and Analysis of Recombinant Adenoviruses for Gene Therapy of Cystic Fibrosis," *Human Gene Therapy* 4(4):461 476 (1993).

Roessler, "Adenoviral–mediated Gene Transfer to Rabbit Synovium In Vivo," *J. Clin. Invest.* 92:1085–1092 (1993).

Roffler, et al., "Anti–neoplastic glucuronide prodrug treatment of human tumor cells targeted with a monoclonal antibody–enzyme conjugate," *Biochem. Pharmacol.* 42(10):2062–2065 (1991).

Sarosy, et al., "Taxol Dose Intensification and its clinical implications," *J. Nat. Med. Assoc.* 85(6):427–431 (1993).

Senter, et al., "Generation of 5–Fluorouracil from 5–Fluorocytosine by Monoclonal Antibody–Cystosine Deaminase Conjugates," *Bioconjugate Chem.* 2(6):447–451 (1991).

Senter, et al., "Generation of Cytotoxic Agents by Targeted Enzymes," *Bioconjugate Chem.* 4(1):3–9 (1993).

Seth, et al., "Role of Low–pH Environment in Adenovirus Enhancement of the Toxicity of a Pseudomonas Exotoxin–Epidermal Growth Factor Conjugate," *J. Virol.* 51(3):650–655 (1984).

Seth, et al., "Evidence that the Penton Base of Adenovirus Is Involved in Potentiation of Toxicity of Pseudomonas Exotoxin Conjugated to Epidermal Growth Factor," *Mol. Cell. Biol.* 4(8):1528–1533 (1984).

Southern, et al., "Transformation of Mammilian Cells to Antibiotic Resitance with a Bacterial Gene Under Control of the SV40 Early Region Promoter," *J. Molec. Appl. Genet.* 1(4):327–341 (1982).

Steinleitner, et al., "Poloxamer 407 as an Intraperitoneal Barrier Material for the Prevention of Postsurgical Adhesion Formation and Reformation in Rodent Models for Reproductive Surgery," *Obstetrics & Gynecology* 77:48–52 (1991).

Steinleitner, et al., "An evaluation of Flowgel as an intraperitonael barrier for prevention of postsurgical adhesion reformation," *Fertility and Sterility* 57(2):305–308 (1992).

Sugsden, et al., "A Vector That Replicates as a Plasmid and Can be Efficiently Selected in B–Lymphoblasts Transformed by the Epstein–Barr Virus," *Mol. Cell. Biol.* 5(2):410–413 (1985).

Svensson, et al., "Role of Vesicles During Adenovirus 2 Internalization into HeLa Cells," *J. Virology* 55(2):442–449 (1985).

Tomita, "Interstitial chemotherapy for brain tumors: review," *J. Neuro–Oncol.* 10:57–74 (1991).

Varga, et al., "Infectious Entry Pathway of Adenovirus Type 2," *J. Virology* 65(11):6061–6070 (1991).

Venditti, et al., "Studies on Oncolytic Agents from Natural Sources. Correlations of Activity Against Animal Tumors and Clinical Effectiveness," *Lloydia* 30(4):332–348 (1967).

Verma, "Retroviral Vectors for Gene Transfer," in Microbiology–1985, American Society for Microbiology, pp. 229–232, Washington, (1985).

Wickham, et al., "Integrins $\alpha_v\beta_3$ and $\alpha_v\beta_5$ Promote Adenovirus Internalization but Not Virus Attachment," *Cell* 73(2):303–319 (1993).

Accadi et al., "Human dystrophin expression in mdx mice after intramuscular injection of DNA constructs," *Nature* 352(6338):815–818 (1991).

Zabner, "Adenovirus–Mediated Gene Transfer Transiently Corrects the Chloride Transport Defect in Nasal Epithelia of Patients with Cystic Fibrosis," *Cell* 75(2):207–216 (1993).

Zabner, "Safety and efficacy of repetitive adenovirus–mediated transfer of CFTR cDNA to airway epithelia of primates and cotton rats," *Nature Genetics* 6(1):75–83 (1994).

Zhang, "Generation and identification of recombinant adenovirus by liposome–mediated transfection and PCR analysis" *BioTechniques* 15(5):868–872 (1993).

METHOD TO ENHANCE TREATMENT OF CYSTIC TUMORS

BACKGROUND OF THE INVENTION

The present invention is generally in the area of delivery vehicles, for therapeutic agents for the treatment of tumors, especially brain tumors, which contain cyst fluid capable of supporting the growth and proliferation of genetically engineered cells.

One-third of all individuals in the United States alone will develop cancer. Although the five-year survival rate has risen dramatically to nearly fifty percent as a result of progress in early diagnosis and therapy, cancer still remains second only to cardiac disease as a cause of death in the United States. Twenty percent of Americans die from cancer, half due to lung, breast, and colon-rectal cancer.

Designing effective treatments for patients with cancer remains a major challenge. The current regimen of surgical resection, external beam radiation therapy, and/or systemic chemotherapy has been partially successful in some kinds of malignancies, but has not produced satisfactory results in others. In some types of brain cancer, such as glioblastoma or multiforme, this multimodality treatment regimen produces a median survival of less than one year. For example, 90% of these treated malignant gliomas recur within two centimeters of the original tumor site within one year.

Though effective in some kinds of cancers, the use of systemic chemotherapy has had minor success in the treatment of cancer of the colon-rectum, esophagus, liver, pancreas, and kidney and melanoma. A major problem with systemic chemotherapy for the treatment of these types of cancer is that the systemic doses required to achieve control of tumor growth frequently result in unacceptable systemic toxicity. Efforts to improve the local delivery of chemotherapeutic agents to the tumor site have resulted in advances in organ-directed chemotherapy, as by continuous systemic infusion, for example. However, continuous infusions of anticancer drugs generally have not shown a clear benefit over pulse or short-term infusions. Implantable elastomer access ports with self-sealing silicone diaphragms have also been tried for continuous infusion, but extravasation remains a problem. Portable infusion pumps are now available as delivery devices and are being evaluated for efficacy (See *Harrison's Principles of Internal Medicine* 431–446, E. Braunwald et al., ed., McGraw-Hill Book Co. (1987) for a general review).

In the brain, the design and development of effective anti-tumor agents for treatment of patients with malignant neoplasms of the central nervous system have been influenced by two major factors: 1) the blood-brain barrier provides an anatomic obstruction in the normal brain, potentially limiting access of drugs to some regions of the tumors; and 2) the antitumor drugs are generally cytotoxic to normal and neoplastic cells alike. Consequently, when the doses of drugs are increased in an attempt to improve intratumoral delivery, the systemic toxicity can be severe. Efforts to improve drug delivery to the tumor bed in the brain have included transient osmotic disruption of the blood brain barrier, cerebrospinal fluid perfusion, local delivery from implanted polymeric controlled release devices and direct infusion into a brain tumor using catheters. Each technique has had significant limitations. Disruption of the blood brain barrier can increase the uptake of hydrophilic substances into normal brain, but may not significantly increase drug delivery into the tumor. Only minimal amounts of agents administered into the cerebrospinal fluid may actually penetrate into the brain parenchyma. Controlled release biocompatible polymers for local drug delivery have been utilized for prevention of ovulation, insulin therapy, glaucoma treatment, asthma therapy, prevention of dental caries, and certain types of cancer chemotherapy (Langer, R., and D. Wise, eds, *Medical Applications of Controlled Release*, Vol. I and II, Boca Raton, CRC Press (1986)). Brain tumors have been particularly refractory to chemotherapy. One of the chief reasons is the restriction imposed by the blood-brain barrier. Agents that appear active against certain brain tumors, such as gliomas, in vitro may fail clinical trials because insufficient drug penetrates the tumor. Although the blood-brain barrier is disrupted at the core of a tumor, it is largely intact at the periphery where cells actively engaged in invasion are located. Experimental intratumoral regimens include infusing or implanting therapeutic agents within the tumor bed following surgical resection (Tomita, T, (*J. Neuro-Oncol.* 10:57–74 (1991)). Drugs that have been used to treat tumors by infusion have been inadequate, did not diffuse an adequate distance from the site of infusion, or could not be maintained at sufficient concentration to allow a sustained diffusion gradient. The use of catheters has been complicated by high rates of infection, obstruction, and malfunction due to clogging (See T. Tomita, *J. Neuro-Oncology* 10:57–74 (1991)).

Delivery of a low molecular weight, lipid soluble chemotherapeutic, 1,3-bis(2-chloroethyl)-1-nitrosourea (BCNU), in a polymer matrix implanted directly adjacent to brain tumors has some efficacy (Brem, et al., *J. Neurosurg.* 74:441–446 (1991); Brem, et al., *Eur. J. Pharm. Biopharm.* 39(1):2–7 (1993); and Brem, et al., *Proc. Amer. Soc. Clin. Oncology* May 17, (1994)). Polymer-mediated delivery of BCNU was superior to systemic delivery in extending survival of animals with intracranial 9L gliosarcoma and has shown some efficacious results in clinical trials. However, BCNU is a low molecular weight drug, crosses the blood-barrier and had previously been demonstrated to have some efficacy when administered systemically. Additionally, acquired drug resistance can result in tumors that become refractory to drugs that were initially effective in controlling tumor growth.

For example, one promising chemotherapeutic, camptothecin, a naturally occurring alkaloid isolate from *Camptotheca acuminata*, a tree indigenous to China, which exerts its pharmacological effects by irreversibly inhibiting topoisomerase I, an enzyme intimately involved in DNA replication, has been shown to have strong cytotoxic anti-tumor activity against a variety of experimental tumors in vitro, such as the L1210 and rat Walker 256 carcinosarcoma (Venditti, J. M., and B. J. Abbott, *Lloydia* 30:332–348 (1967); Moertel, C. G., et al., *Cancer Chemother. Rep.* 56(1):95–101 (1972)). Phase I and II clinical trials of camptothecin in human patients with melanoma and advanced gastrointestinal carcinoma, however, have shown unexpectedly severe systemic toxicity with poor tumoral responses, and clinical investigation therefore halted (Gottlieb, J. A., and J. K. Luce, *Cancer Chemother. Rep.* 56(1):103–105 (1972); Moertel, C. G., et al., *Cancer Chemother. Rep.* 56(1):95–101 (1972); Muggia, F. M., et al., *Cancer Chemother. Rep.* 56(4):515–521 (1972)). Many other chemotherapeutics which are efficacious when administered systemically must be delivered at very high dosages in order to avoid toxicity due to poor bioavailability. For example, paclitaxel (taxol) has been used systemically with efficacy in treating several human tumors, including ovarian, breast, and non-small cell lung cancer. However, maintenance of sufficient systemic levels of the drug for treatment of tumors has been associated with severe, in some cases "life-threatening" toxicity (Sarosy and Reed, *J. Nat. Med. Assoc.* 85(6):427–431 (1993)). Paclitaxel is a high molecular weight (854), highly lipophilic deterpenoid isolated from the western yew, *Taxus brevifolia*, which is insoluble in water. It is normally administered intravenously by dilution into saline of the drug dissolved or suspended in polyoxyethylated castor oil. This carrier has been reported to induce an anaphylactic reaction in a number of patients (Sarosy and Reed (1993)) so alternative carriers have been proposed, such as a mixed micellar formulation for parenteral administration (Alkan-Onyuksel, et al., *Pharm. Res.* 11(2), 206–212 (1994)).

Gene transfer is rapidly becoming a useful adjunct in the development of new therapies for human malignancy. Tumor cell expression of histocompatibility antigens, cytokines, or growth factors (e.g., IL-2, IL-4, GMCSF) appears to enhance immune-mediated clearance of malignant cells in animal models, and expression of chemoprotectant gene products, such as p-glycoprotein in autologous bone marrow cells, is under study as a means of minimizing marrow toxicity following administration of otherwise lethal doses of chemotherapeutic agents.

Theoretically, the most direct mechanism for tumor cell killing using gene transfer is the selective expression of cytotoxic gene products within tumor cells. Classical enzymatic toxins such as pseudomonas exotoxin A, diphtheria toxin and ricin are unlikely to be useful in this context, since these enzymes kill only cells in which they are expressed, and no current gene transfer vector is capable of gene delivery to a sufficiently high percentage of tumor cells to make use of the above recombinant enzymes.

Another strategy that has been developed to selectively kill tumor cells involves the delivery to replicating tumor cells and expression of genes encoding enzymes such as the Herpes simplex virus thymidine kinase (HSV-tk) gene followed by treatment with a prodrug activated by this enzyme such as ganciclovir. Ganciclovir is readily phosphorylated by the HSV-tk, and its phosphorylated metabolites are toxic to the cell. Very little phosphorylation of ganciclovir occurs in normal human cells. Although only those cells expressing the HSV-tk should be sensitive to ganciclovir (since its phosphorylated metabolites do not readily cross cell membranes), in vitro and in vivo experiments have shown that a greater number of tumor cells are killed by ganciclovir treatment than would be expected based on the percentage of cells containing the HSV-tk gene. This unexpected result has been termed the "bystander effect" or "metabolic cooperation". It is thought that the phosphorylated metabolites of ganciclovir may be passed from one cell to another through gap junctions.

Although the bystander effect has been observed in initial experiments using HSV-tk, the limitations present in all current gene delivery vehicles mean that a much greater bystander effect than previously noted will be important to successfully treat human tumors using this approach. One of the difficulties with the current bystander toxicity models is that bystander toxicity with metabolites that do not readily cross the cell membrane will not be sufficient to overcome a low efficiency of gene transfer (e.g., transfection, transduction, etc.). In the known toxin gene therapy systems, the efficiency of transduction and/or transfection in vivo is generally low. An existing protocol for treating brian tumors in humans uses retroviral delivery of HSV-tk, followed by ganciclovir administration. In rat models using 9L cells, a solid glial sarcoma cell line, using HSV-tk in this context, tumor regressions have been observed (Culver, et al., *Science*, 256:1550–1552 (1992)). This HSV-tk approach is under investigation for treatment of patients with brain, head and neck, and ovarian tumors.

Similarly, the usefulness of *E. coli* cytosine deaminase (which converts 5-fluorocytosine to 5-fluorouracil and could theoretically provide substantial bystander toxicity) in this regard remains to be established. Initial studies have shown that cytosine deaminase expression followed by treatment with 5-fluorocytosine in clonogenic assays leads to minimal bystander killing (Mullen et al., *Proc. Natl. Acad. Sci. USA*, 89:33–37 (1992)).

Prodrug activation by an otherwise non-toxic enzyme (e.g., HSV-tk, cytosine deaminase) has advantages over the expression of directly toxic genes, such as ricin, diphtheria toxin, or pseudomonas exotoxin. These advantages include the capability to titrate cell killing, optimize therapeutic index by adjusting either levels of prodrug or of recombinant enzyme expression, and interrupt toxicity by omitting administration of the prodrug. However, like other recombinant toxic genes, gene transfer of HSV-tk followed by treatment with ganciclovir is neither optimized to kill bystander cells nor is it certain bystander toxicity will occur in vivo as has been characterized in vitro. An additional problem with the use of the HSV-tk or cytosine deaminase to create toxic metabolites in tumor cells is the fact that the agents activated by HSV-tk (ganciclovir, etc.) and cytosine deaminase (5-fluorocytosine) will kill only cells that are synthesizing DNA (Balzarini, et al., *J. Biol. Chem.*, 268:6332–6337 (1993), and Bruce and Meeker, *J. Natl. Cancer Inst.*, 38:401–405 (1967)). Even if a considerable number of nontransfected cells are killed, one would not expect to kill the nondividing tumor cells with these agents.

It is therefore an object of the present invention to provide vehicles that increase the efficiency of delivery of therapeutic reagents, including viral vectors, cells, nucleic acids, antibodies and other proteins, lipids, and carbohydrates, to tumors, especially brain tumors.

It is a further object of the present invention to provide methods for enhancing delivery of genetic materials to encapsulated tumors.

SUMMARY OF THE INVENTION

It has been discovered that cells such as genetically engineered fibroblasts and keratinocytes can be cultured in the cyst fluid of encapsulated tumors. This provides a means for proliferating genetically engineered producer cells within these types of tumors, increasing the number of cells producing viral particles, which then transduce the surrounding tumor cells with the genetic material, in the preferred embodiment, a lethal gene. As used herein, a "lethal" gene is a gene which can be used to kill specific cells, usually tumor cells. An example of a lethal gene is the gene encoding the herpes simplex virus thymidine kinase enzyme. Subsequent treatment of a cell expressing the thymidine kinase enzyme with ganciclovir results in cell death. A lethal gene can also encode an oligonucleotide such as a ribozyme-type molecule or antisense molecule which interfere with an essential function of the cell. Alternatively, a lethal gene can encode a protein(s) which stimulates or activates the patient's own immune system to attack the tumor. Techniques for genetically engineering the producer cells, and reagents for engineering the cells, are known. A number of different tumor types form "cysts", which contain fluid produced by the tumor cells, including brain tumor cells such as gliomas, and many types of breast, and lung tumors. These cyst fluids have been shown to contain elevated levels of certain growth factors, for example, fibroblast growth factor (FGF) and epidermal growth factor (EGF). The types of genetically engineered cells to be used can be selected in part according to the levels of growth factors in the cyst fluid which most promote growth of the cells, for example, cystic tumors with high levels of FGF would be injected with genetically engineered fibroblasts; cystic tumors with high levels of EGF would be injected with genetically engineered keratinocytes; and cystic tumors with high levels of vascular endothelial growth factor (VEGF) would be injected with genetically engineered endothelial cells.

Examples demonstrate proliferation of fibroblasts in cyst fluid of gliomas, with transfer of genetic material by diffusion through the cyst fluid into adjacent tumor cells, and that retroviral transduced fibroblast producer cells transfer genetic materials from virus producing cells encapsulated with Matrigel to tumor cells.

DETAILED DESCRIPTION OF THE INVENTION

Solid tumors secrete a number of proteins that can stimulate other cell types to proliferate, i.e., fibroblast growth factor, or affect the function of nearby cells, i.e., vascular endothelial growth factor induced permeability of blood vessels adjacent to tumors. Some tumors actually form cysts that are composed of membranes made up of normal and neoplastic cells that surround collections of fluids of varying compositions. For example, malignant glioma brain tumors have been shown to contain basic fibroblast growth factor and vascular endothelial growth factor while craniopharyngioma cysts typically contain cholesterol deposits. Depending on their size and location, cystic tumors cause clinically significant problems by compressing adjacent tissue that can impair organ function or by releasing substances that adversely affects the surrounding tissue. Techniques have been developed to drain cystic tumors and instill drugs or radionuclides into the cyst. While sometimes effective, these approaches are of limited efficacy because the cysts often recur, permanently implanted catheters often become occluded and are a source of infection, and toxic molecules can extravasate from a cyst and injure surrounding tissues.

Cystic Tumors

This method involves selection and treatment of cystic tumors. Cystic tumors are a type of tumor which is generally encapsulated and produces within the tumor a cyst fluid that tends to collect within a fibrous membrane or tumor cell lined pocket in the interior of the tumor. In the brain, these cystic tumors commonly include the intrinsic brain tumors such as gliomas, astrocytomas, craniopharyngiomas, meningiomas, pituitary adenomas, hemangioblastomas, and the metastatic tumors of lung, breast, kidney, gastrointestinal, and melanocytic cell organs.

Materials to be Delivered

The materials to be delivered to the cystic tumor generally include genetically engineered cells, which may be injected directly into the cyst fluid in a buffer or nutrient solution, or in a carrier vehicle enhancing retention of the genetically engineered materials within the tumor. These are discussed in more detail below.

Genetic Materials

As used herein, a "lethal" gene is a gene which can be used to kill specific cells, usually tumor cells. An example of a lethal gene is the gene encoding the herpes simplex thymidine kinase (HSV-tk). Subsequent treatment of the cells that express HSV-tk with ganciclovir leads to cytotoxicity. A lethal gene can also encode an oligonucleotide such as a ribozyme-type molecule or antisense molecule which interferes with an essential function of the cell. Alternatively, a lethal gene can encode a protein(s) which stimulates or activates the patient's own immune system to attack the tumor. In the latter case, this could even be viral vector proteins, which are known to be immunogenic, or materials such as interleukins 8 or 10 which diminish the immune response. These materials are collectively referred to as "genetically engineered materials" Genetically engineered materials include RNA or DNA encoding a toxin, ribozymes, external guide sequences for RNAase P, antisense, triplex forming oligonucleotides, selective or targeted mutagens, and combinations thereof.

Cells to be Genetically Engineered and Delivered to Tumors

Many types of cells can be transfected using these techniques and reagents. Preferred cell types for treatment of brain tumors include fibroblasts, keratinocytes, and endothelial cells. Bone progenitor cells or differentiated cells such as osteoblasts can also be used. Bone marrow stem cells and hematopoietic cells are relatively easily removed and replaced from humans, and provide a self-regenerating population of cells for the propagation of transferred genes. The cells are selected according to the type of tumor to be treated, the contents of the cyst fluid, the molecular characteristics of the tumor, as well as the genetically engineered material to be delivered. When in vitro transfection of cells is performed, once the transfected cells begin producing the proteins encoded by the genes, the cells can be added back to the patient to establish entire pooled populations of cells that are expressing the transfected genes.

The types of genetically engineered cells to be used can be selected in part according to the levels of growth factors in the cyst fluid which most promote growth of the cells, for example, cystic tumors with high levels of FGF would be injected with genetically engineered fibroblasts; cystic tumors with high levels of EGF would be injected with genetically engineered keratinocytes; and cystic tumors with high levels of vascular endothelial growth factor (VEGF) would be injected with genetically engineered endothelial cells.

Methods and Reagents for Transfer of Genetic Material

Gene transfer can be obtained using direct transfer of genetic material, in a plasmid or viral vector, or via transfer of genetic material in cells or carriers such as cationic liposomes. Such methods are well known in the art and readily adaptable for use in the gene mediated toxin therapies described herein. Further, these methods can be used to target certain diseases and cell populations by using the targeting characteristics of the carrier. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83–88, (1993)). Appropriate means for transfection, including viral vectors, chemical transfectants, or physico-mechanical methods such as electroporation and direct diffusion of DNA, are described by, for example, Wolff, J. A., et al., *Science,* 247, 1465–1468, (1990); and Wolff, J. A. *Nature,* 352, 815–818, (1991).

As used herein, plasmid or viral vectors are agents that transport the gene into the cell without degradation and include a promoter yielding expression of the gene in the cells into which it is delivered. In a preferred embodiment vectors are derived from either a virus or a retrovirus. Preferred viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Preferred retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors have higher transaction (ability to introduce genes) abilities than do most chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In MICROBIOLOGY-1985, American Society for Microbiology, pp. 229–232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (*Science* 260:926–932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

Adenoviral Vectors

The construction of replication-defective adenoviruses has been described (Berkner et al., *J. Virology* 61:1213–1220 (1987); Massie et al., *Mol. Cell. Biol.* 6:2872–2883 (1986); Haj-Ahmad et al., *J. Virology* 57:267–274 (1986); Davidson et al., *J. Virology* 61:1226–1239 (1987); Zhang "Generation and identification of recombinant adenovirus by liposome-mediated transfection and PCR analysis" *BioTechniques* 15:868–872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580–1586 (1993); Kirshenbaum, *J. Clin. Invest.* 92:381–387 (1993); Roessler, *J. Clin. Invest.* 92:1085–1092 (1993); Moullier, *Nature Genetics* 4:154–159 (1993); La Salle, *Science* 259:988–990 (1993); Gomez-Foix, *J. Biol. Chem.* 267:25129–25134 (1992); Rich, *Human*

Gene Therapy 4:461–476 (1993); Zabner, *Nature Genetics* 6:75–83 (1994); Guzman, *Circulation Research* 73:1201–1207 (1993); Bout, *Human Gene Therapy* 5:3–10 (1994); Zabner, *Cell* 75:207–216 (1993); Caillaud, *Eur. J. Neuroscience* 5:1287–1291 (1993); and Ragot,*J. Gen. Virology* 74:501–507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462–477 (1970); Brown and Burlingham, *J. Virology* 12:386–396 (1973); Svensson and Persson, *J. Virology* 55:442–449 (1985); Seth, et al., *J. Virol.* 51:650–655 (1984); Seth, et al., *Mol. Cell. Biol.* 4:1528–1533 (1984); Varga et al.,*J. Virology* 65:6061–6070 (1991); Wickham et al., *Cell* 73:309–319 (1993)).

A preferred viral vector is one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355–360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell 33: 729* (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus. Preferred examples are the SV40 enhancer on the late side of the replication origin (bp 100–270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

It is preferred that the promoter and/or enhancer region act as a constitutive promoter and/or enhancer to maximize expression of the region of the transcription unit to be transcribed. It is further preferred that the promoter and/or enhancer region be active in all eukaryotic cell types. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases (FIG. 1). It is also preferred that the transcribed units contain other standard sequences alone or in combination with the above sequences improve expression from, or stability of, the construct.

Markers

The viral vectors can include nucleic acid sequence encoding a marker product. This marker product is used to determine if the gene has been delivered to the cell and once delivered is being expressed. Preferred marker genes are the *E. Coli* lacZ gene which encodes b-galactosidase and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410–413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Carriers

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447–451, (1991); Bagshawe, K. D., *Br. J. Cancer,* 60:275–281, (1989); Bagshawe, et al., *Br. J. Cancer,* 58:700–703, (1988); Senter, et al., *Bioconjugate Chem.*, 4:3–9, (1993); Battelli, et al., *Cancer Immunol. Immunother.*, 35:421–425, (1992); Pietersz and McKenzie, *Immunolog. Reviews,* 129:57–80, (1992); and Roffler, et al., *Biochem. Pharmacol,* 42:2062–2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214–6220, (1989); and Litzinger and Huang, *Biochimica et Biophysica Acta,* 1104:179–187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399–409 (1991)).

As discussed above, a strategy that has been developed to selectively kill tumor cells involves the delivery to replicating tumor cells and expression of genes encoding toxic prodrugs such as the HSV-tk gene followed by treatment with ganciclovir. Ganciclovir is readily phosphorylated by the HSV-tk, and its phosphorylated metabolites are toxic to the cell. Very little phosphorylation of ganciclovir occurs in normal human cells. Examples of other genetically engineered cells that can be delivered as described herein include cells transfected with the *E. coli* Deo D gene (purine nucleoside phosphorylase (PNP)) and subsequently treating with a nontoxic nucleoside analog (e.g., deoxyadenosine or deoxyguanosine analogs, including N7 analogs), which is converted to a toxic purine analog. *E. coli* PNP differs from human PNP in its acceptance of adenine- and certain guanine-containing nucleoside analogs as substrates. *E. coli* PNP expressed in tumor cells cleaves the nucleoside, liberating a toxic purine base analog. Purine bases freely diffuse across cell membranes, whereas nucleoside monophosphates generally remain inside the cell in which they are formed. The substrate administered to the cells is 9-(β-D-2-deoxyerythropentofuranosyl)-6-methylpurine (MeP-dR). A toxic adenine analog formed after conversion by *E. coli* PNP can be converted by adenine phosphoribosyl transferase to toxic nucleotides and kill all transfected cells, and diffuse out of the cell and kill surrounding cells that were not transfected (bystander cells).

Density or Viscosity Modifying Materials

A variety of materials are known which can be adapted for use in the method described herein. It is not required that the material be biocompatible if the treatment is designed to kill tumors; for example, a vehicle which includes a cytotoxic compound such as ethanol may be used to facilitate delivery and efficacy of a chemotherapeutic agent to tumors.

Preferred materials are polymers which solidify or gel at the site of delivery. Polymeric solutions or suspensions can be formulated which solidify by formation of ionic or covalent coupling of the polymer, for example, through interactions with cations such as calcium, changes in pH, changes in temperature, and polymerization.

Polymer Solutions

The polymeric material which is mixed with cells or other materials for injection into the body should preferably form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Naturally occurring and synthetic hydrogel forming polymers, polymer mixtures and copolymers may be utilized as hydrogel precursors. Examples of materials which can be used to form a hydrogel include polysaccharides such as alginate and modified alginates, synthetic polymers such as polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

Natural Polymer Solutions

In one embodiment, the polymers are natural polymers such as proteins and polysaccharides. In the preferred embodiment, the protein solution is cryoprecipitate or fibrinogen derived from the patient to be treated. Proteins and polysaccharides can be ionically linked, typically by the addition of cations, crosslinked chemically for example using glutaraldehyde, or by chemical denaturation.

In a particularly preferred embodiment, cryoprecipitate is prepared from a plasma sample obtained directly from the patient. One unit of human blood consists of approximately 350 to 450 mls, which is preferably collected in ACD (citric acid-dextrose) anticoagulant, although other acceptable anticoagulants can be used such as ethylene diamine tetraacetate. The red blood cells are removed by centrifugation or filtration, and the separated plasma chilled at 4 C until cryoprecipitate is formed, typically about three days. Cryoprecipitate consists predominantly of fibrinogen. Fresh frozen plasma can also be used.

Purified fibrinogen is also available from commercial suppliers such as Sigma Chemical Co., Baxter Diagnostics, and Ortho Pharmaceuticals. As used herein, the term "fibrinogen" is intended to encompass either cryoprecipitate or purified fibrinogen, unless specifically stated otherwise. Other materials that can be used as a source of fibrinogen besides cryoprecipitate, fresh frozen plasma, and purified fibrinogen, include factor VIII concentrate, platelet concentrate, and platelet rich plasma. Proteins other than fibrinogen can be substituted for the fibrinogen where the protein can be prepared and crosslinked using a physiologically acceptable crosslinker such as calcium. Crosslinking may be improved by addition of factor XIII. An advantage of the fibrinogen is that it is readily obtained in sufficient quantities merely by drawing blood from the intended recipient so that there is no problem with patient rejection of the implant or introduction of infectious agents harbored by the fibrinogen donor.

Alginate is a carbohydrate polymer isolated from seaweed, which can be crosslinked to form a hydrogel by exposure to a divalent cation such as calcium, as described, for example in WO 94/25080, the disclosure of which is incorporated herein by reference. Alginate is ionically crosslinked in the presence of divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Examples of other materials which can be used to form a hydrogel include modified alginates. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemical modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or $\epsilon$-caprolactone. The resulting polymer includes alginate blocks which permit ionically catalyzed gelling, and oligoester blocks which produce more rapid degradation depending on the synthetic design. In the embodiment wherein modified alginates and other anionic polymers that can form hydrogels which are malleable are used to encapsulate cells, the hydrogel is produced by cross-linking the polymer with the appropriate cation, and the strength of the hydrogel bonding increases with either increasing concentrations of cations or of polymer. Concentrations from as low as 0.001 M have been shown to cross-link alginate. Higher concentrations are limited by the toxicity of the salt. Alternatively, alginate polymers may be used, wherein the ratio of mannuronic acid to glucuronic acid does not produce a firm gel, which are derivatized with hydrophobic, water-labile chains, e.g., oligomers of $\epsilon$-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Other natural materials include hydroxyapatite, coral, calcium carbonate, and other polymer or aggregates which are useful in inducing or enhancing the growth and proliferation of cells forming bone, especially osteoblasts. These materials can be delivered in combination with genetically engineered osteoblasts into tumors such as prostrate tumors which also form gap junctions, to enhance the intercellular transfer of small molecules, such as ganciclovir, and metabolites, from osteoblasts to the tumor cells.

Synthetic Ionically Cross-Linkable Polymers

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups. Methods for the synthesis of the polymers described above are known to those skilled in the art. (See, for example *Concise Encyclopedia of Polymer Science* and *Polymeric Amines and Ammonium Salts*, E. Goethals, editor, Pergamen Press, Elmsford, N.Y. (1980)). Many polymers, such as poly(acrylic acid), are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. Examples of cations for cross-linking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. The preferred cations for cross-linking of the polymers with acidic side groups to form a hydrogel are divalent and trivalent cations such as copper, calcium, aluminum, magnesium, strontium, barium, and tin. Aqueous solutions of the salts of these cations are added to the polymers to form soft, highly swollen hydrogels and membranes. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Synthetic Polymers Crosslinkable by Hydrogen Bonding

Other polymeric hydrogel precursors include polyethylene oxide-polypropylene glycol block copolymers such as Pluronics™ or Tetronics™, which are crosslinked by hydrogen bonding and/or by a temperature change (Steinleitner et al., *Obstetrics & Gynecology*, 77:48–52 (1991); and Steinleitner et al., *Fertility and Sterility* 57:305–308 (1992)).

Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Synthetic Covalently Crosslinkable Polymers

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized (Matsuda et al., *ASAID Trans.*, 38:154–157 (1992)).

Density Modifying Agents

Although described herein particularly with reference to polymers which increase the viscosity and/or density of the material to be injected into the tissue to be treated, other materials could also be used which are not polymers. Many agents which increase viscosity or density are routinely used, especially in the food and medical industry. Generally, these include proteins such as albumin, sugars such as dextran, glucose and fructose, and starches, although these are technically polymers. As used herein, the term "polymers" encompasses the addition of monomers or single unit material that function to increase the viscosity and/or density of the solution to be injected into the tissue to be treated.

Polysaccharides that are very viscous liquids or are thixotropic, and form a gel over time by the slow evolution of structure, are especially useful. For example, hyaluronic acid, which forms an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other materials that are dense and/or viscous include many of the lipids and sterols such as cholesterol, oils and fats.

Cell Suspensions

Preferably the polymer or density modifying agent is dissolved in an aqueous solution, preferably a 0.1 M potassium phosphate solution, at physiological pH, to a concentration yielding the desired density, for example, for alginate, of between 0.5 to 2% by weight, preferably 1%, alginate. The isolated cells are suspended in the polymer solution to a concentration of between 1 and 100 million cells/ml, most preferably approximately 100 million cells/ml. In a preferred embodiment, the polymer is fibrinogen and the cells are added to one ml of commercially available thrombin to a concentration of 100 million cells, then added to an equivalent volume of fibrinogen for injection into the tumor.

Combinations of materials increasing viscosity and density, as described above, may also be utilized.

Additives

A variety of materials can be added to the polymer-cell solution. Examples of useful materials include proteins, polysaccharides, nucleic acids, vitamins and metals or ions (calcium, sodium and potassium), and synthetic organic molecules. Examples include enzymes such as collagenase inhibitors, hemostatic agents such as thrombin, fibrinogen or calcium ions, growth factors, angiogenic factors and other growth effector molecules, bacteriostatic or bacteriocidal factors, antiinflammatories, anti-angiogenic agents, and vitamins. Growth effector molecules, as used herein, refer to molecules that bind to cell surface receptors and regulate the growth, replication or differentiation of target cells or tissue. Preferred growth effector molecules are growth factors and extracellular matrix molecules. Examples of growth factors include epidermal growth factor (EGF), platelet-derived growth factor (PDGF), transforming growth factors (TGFá, TGFâ), hepatocyte growth factor, heparin binding factor, insulin-like growth factor I or II, fibroblast growth factor (FGF), VEGF, LPA, erythropoietin, nerve growth factor, bone morphogenic proteins, muscle morphogenic proteins, and other factors known to those of skill in the art. Additional growth factors are described in "Peptide Growth Factors and Their Receptors I" M. B. Sporn and A. B. Roberts, eds. (Springer-Verlag, N.Y., (1990)), for example, the teachings of which are incorporated by reference herein. Growth factors which are preferred when the material to be injected is fibroblasts, especially skin fibroblasts, are EGF and FGF. Many growth factors are also available commercially from vendors, such as Sigma Chemical Co. of St. Louis, Mo., Collaborative Research, Genzyme, Boehringer, R&D Systems, and GIBCO, in both natural and recombinant forms. Examples of extracellular matrix molecules include fibronectin, laminin, collagens, and proteoglycans. Other extracellular matrix molecules are described in Kleinman et al. (1987) or are known to those skilled in the art. Other growth effector molecules include cytokines, such as the interleukins and GM-colony stimulating factor, and hormones, such as insulin. These are also described in the literature and are commercially available. Collagenase inhibitors, including tissue inhibitor metalloproteinase (TIMP), may also be useful as growth effector molecules.

Examples of hemostatic agents include thrombin, Factor Xa, fibrinogen, and calcium ions, typically in the form of calcium chloride or calcium gluconate. Vasoconstrictive agents such as epinephrine can also be used to contract blood vessels and thereby decrease bleeding. Bacteriostatic and bacteriocidal agents include antibiotics and other compounds used for preventing or treating infection in wounds.

The present invention will be further understood by reference to the following non-limiting examples.

EXAMPLE 1

Transduction of Human Glioma Cell Lines Growing in Human Brain Tumor Cyst Fluid

Materials and Methods

Brain tumor cyst fluids were obtained at the time of surgery by aspiration of cyst contents after puncture of the cyst with a 18 gauge angiocatheter connected to a 10 cc syringe. Aliquots were placed in NUNC™ cyrovials, frozen and stored at −80° C. The cyst fluid was thawed prior to use.

The U87 and U 343 glioma cells were seeded into 24 well tissue culture plates at densities of $1 \times 10^4$ cells/50 $\mu$L. 200 $\mu$L of brain tumor cyst fluid (TCF), normal media or fetal bovine serum (FBS) were then added to each well. Tissue culture inserts (Falcon) with 0.25 micron pores were then paced into each experimental well. Into each insert of the experimental wells, $1 \times 10^5$ HyTk vector (Targeted Genetics, Seattle, Wash.) producing fibroblasts (VPC) were seeded. Control wells consisted of inserts with no VPC. The cells were incubated at 37° C. at 5% $CO_2$ for four days. The inserts were then removed, the tumor cells washed with normal media, and cultured in normal media for 48 hours. VPC growing in the inserts were trypsinized and passaged into normal media. Media containing 600 $\mu$g/ml of hygromycin was then added to the glioma cells and they were incubated as above.

Results

One week later, there were no viable cells in the control wells; however, there were viable cells present in the wells of normal media, tumor cyst fluid, or FBS that had exposed to VPC. These cells were passaged and then seeded in 12 well plates at densities of $5 \times 10^5$ cells/well. One day later a dose response test was performed to the drug ganciclovir (GCV). The drug was added at concentrations of 1, 10, and 100 $\mu$M GCV. Viable cells were counted by the trypan blue exclusion method and recorded. Untransduced U87 control cells were also grown at each dose of the GCV drug. The results for U87 dose response experiment are shown in FIGS. 1a, 1b, 2 and 3.

Figure 1A:
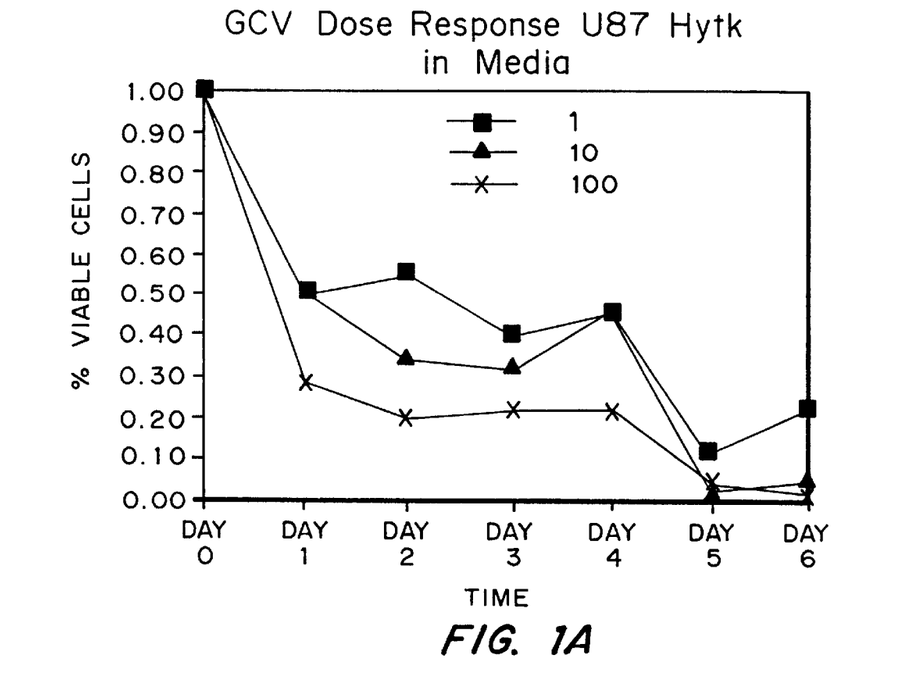
FIGS. 1a and 1b are graphs of the ganciclovir dose response of U87 tumor cells transduced with HSV-tk (FIG. 1a) or control cells not transduced (FIG. 1b) in media, following treatment with 1, 10 or 100 $\mu$M ganciclovir, over a period of six days.
Figure 1B:
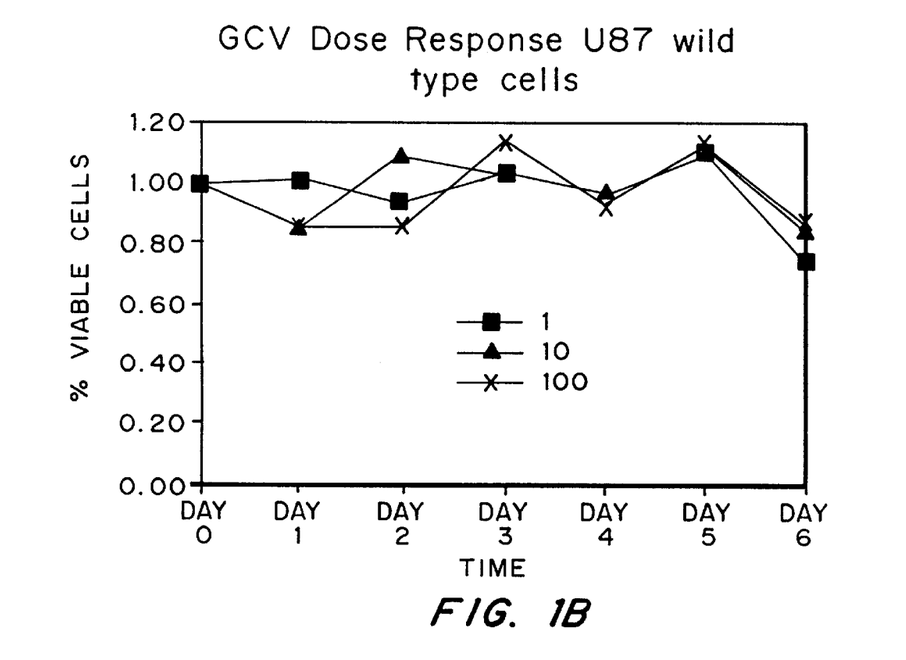
Figure 2:
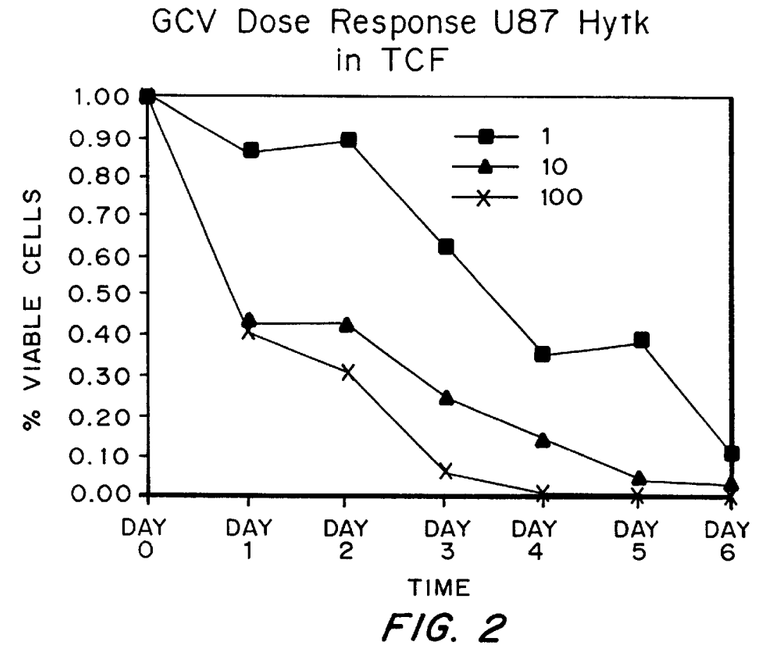
FIG. 2 is a graph of the ganciclovir dose response of U87 tumor cells transduced with HSV-tk in tumor cyst fluid (TCF), following treatment with 1, 10 or 100 $\mu$M ganciclovir, over a period of six days.
Figure 3:
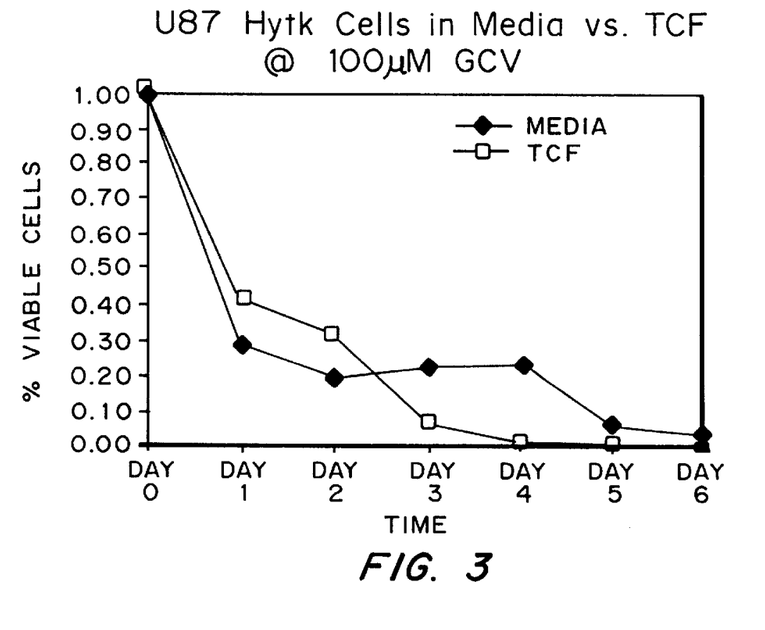
FIG. 3 is a graph comparing the response of U87 tumor cells transduced with HSV-tk, in either media or TCF, following treatment with 100 $\mu$M ganciclovir, over a period of six days.

FIG. 1a is the ganciclovir (GCV) dose response curve, comparing efficacy of the drug at 1, 10 and 100 $\mu$M over six days in cell culture media. As is evident from the figure, the percent viable cells declines at all dosages tested, to almost zero at 10 and 100 $\mu$M GCV. FIG. 1b shows the control cells in media. FIG. 2 is the GCV dose response in U87 cells in TCF. FIG. 3 compares killing of U87 (percent viable cells) over time in either media or TCF in the presence of 100 $\mu$M GCF.

These experiments demonstrate that retroviral vector producing fibroblasts can survive in human brain tumor cyst fluid and that tumor cells not in direct contact with the VPC can be transduced, as evidenced by the survival of tumor cells in hygromycin containing media. These tumor cells were then shown to be sensitive to three different doses of GCV that the control cells were unaffected by. After growth in the cyst fluid for 7 days, the VPC could be trypsinized and passaged, demonstrating their viability. These results demonstrate that retroviral vector mediated gene transfer to neoplastic cells can occur in tumor cyst fluid.

EXAMPLE 2

Transduction of Glioma Cell Lines with HyTk Retroviral Vector Conditioned Matrigel Materials and Methods $10^5$ Retroviral vector producing fibroblasts (VPC) were suspended into 200 μL of Eagles modified essential media (Emem) supplemented with 10% fetal bovine serum (FBS) and seeded into wells of 12 well plates (Falcon). 600 μL Matrigel (Becton Dickinson) at 4° C. was then immediately added to each experimental well. Controls consisted of VPC seeded in normal media alone.

Cells were incubated at 37° C. at 5% $CO_2$ for four days. The matrigel was then dissolved by adding 2 mL of media at 4° centigrade, resuspended and sterilely filtered through 0.25 micron filters. This media—matrigel filtrate was then added to the wells of U87, T98G, or U343 glioma cells that had been seeded in 12 well plates at densities of $5\times10^4$ cells/well, 2 hours earlier. They were incubated as above for four days, washed with normal media, and then media containing 600 μg/ml of hygromycin was added. Controls consisted of these tumor cells that were treated with media containing 600 μg/ml of hygromycin alone, without exposure to the retroviral vector conditioned matrigel.

Results

One week later viable tumor cells were present in every well exposed to the retroviral vector conditioned matrigel, as compared to the control wells which contained no viable cells. This experiment demonstrates that VPC can survive for 4 days and replicate in matrigel and that the matrigel conditioned in this manner can successfully transduce target neoplastic cells, as evidenced by their survival in hygromycin.

EXAMPLE 3

Transduction of U87 and BT474 Neoplastic Cells

Materials and Methods

U87 and BT474 neoplastic cells were seeded in tissue culture plates at a density of 10,000 cells/well, and grown in Eagle's modified essential media supplemented with 10% fetal bovine serum. Initially, the cells seeded in precisely the same manner with the exception that the cells were grown in human glioma and human breast cancer cyst fluid instead of normal media. Viral stocks providing for a multiplicity of infection of $5\times10^3$ were added to each well. Control cells had no virus added. The cells were incubated at 37° C. at 5% $CO_2$. Twenty four hours later the media or tumor cyst fluid was aspirated, the cells washed with normal media and then normal saline was added to each well. Cells were then viewed in a fluorescent microscope at a wavelength of 488.

Results

Green cells were identified in the wells containing U87 cells growing in the normal media and tumor cyst fluid and BT474 breast cancer cells growing in normal media and tumor cyst fluid. There was no evidence of green fluorescence in any of the control cells.

Modifications and variations of the present invention will be obvious to those skilled in the art from the foregoing detailed description. Such modifications and variations are intended to come within the scope of the appended claims.

I claim:

1. A method for delivery of genetic material or the product thereof to the cells of a cystic tumor comprising
   injecting the genetic material into the tumor cyst fluid within the cystic tumor,
   wherein the genetic material or product expressed from the genetic material is present in the tumor cyst fluid in an amount effective to kill cystic tumor cells.

2. The method of claim 1 further comprising adding to the genetic material prior to injection into the tumor cyst fluid a vehicle having a consistency and density effective to retain the genetic material at the site of injection.

3. The method of claim 1 wherein the genetic material is delivered into the tumor cyst fluid in genetically engineered cells selected from the group consisting of fibroblasts, endothelial cells, keratinocytes, and bone progenitor or differentiated cells.

4. The method of claim 1 wherein the genetic material includes a viral vector selected from the group consisting of adenoviral vectors, adeno-associated viral vectors, and retroviral vectors.

5. The method of claim 1 wherein the cystic tumor is selected from the group consisting of gliomas, astrocytomas, craniopharyngiomas, meningiomas, pituitary adenomas, hemangioblastomas, metastatic tumors of lung, metastatic tumors of breast, metastatic tumors of kidney, metastatic tumors of the gastrointestinal tract, and melanocytic cell tumors.

6. The method of claim 2 wherein the genetic material contains recombinant nucleic acid material selected from the group consisting of viral vector genes, genes encoding a protein, ribozymes, external guide sequences for RNAase P, antisense oligonucleotides, triplex forming oligonucleotides, mutagens, and combinations thereof.

7. The method of claim 3 further comprising analyzing the tumor cyst fluid for growth factors and selecting the type of cells to be genetically engineered based on the type of growth factors present in the tumor cyst fluid.

8. The method of claim 3 wherein the tumor cyst fluid contains vascular endothelial growth factor and the genetically engineered cells are endothelial cells.

9. The method of claim 3 wherein the tumor cyst fluid contains fibroblast growth factor and the genetically engineered cells are fibroblasts.

10. The method of claim 3 wherein the tumor cyst fluid contains epithelial growth factor and the genetically engineered cells are keratinocytes.

11. The method of claim 3 further comprising the step of genetically engineering the cells prior to injection into the tumor cyst fluid to stimulate or activate cells of the immune system to kill the tumor cells.

12. The method of claim 6 wherein the recombinant nucleic acid material is in a carrier selected from the group consisting of a plasmid and a viral vector.

13. An isolated composition for delivery of genetic material into cystic tumor cells comprising genetically engineered cells in tumor cyst fluid.

14. The composition of claim 13 further comprising a vehicle having a consistency and density effective to retain the genetically engineered cells at the site where the genetically engineered cells are delivered.

15. The composition of claim 13 wherein the genetically engineered cells contain recombinant nucleic acid material selected from the group consisting of viral vector genes, genes encoding a protein, ribozymes, external guide sequences for RNAase P, antisense oligonucleotides, triplex forming oligonucleotides, mutagens, and combinations thereof.

16. The composition of claim 13 wherein the genetically engineered cells are selected from the group consisting of fibroblasts, endothelial cells, keratinocytes, and bone progenitor or differentiated cells.

17. The composition of claim 13 wherein the tumor cyst fluid contains vascular endothelial growth factor and the genetically engineered cells are endothelial cells.

18. The composition of claim 13 wherein the tumor cyst fluid contains fibroblast growth factor and the genetically engineered cells are fibroblasts.

19. The composition of claim 13 wherein the tumor cyst fluid contains epithelial growth factor and the genetically engineered cells are keratinocytes.

20. The composition of claim 13 wherein the cells are genetically engineered prior to injection into the tumor cyst fluid to stimulate or activate cells of the immune system to kill tumor cells.

21. The composition of claim 15 wherein the recombinant nucleic acid material is in a carrier selected from the group consisting of a plasmid and a viral vector.

22. The composition of claim 21 wherein the genetically engineered cells contain a viral vector selected from the group consisting of adenoviral vectors, adeno-associated viral vectors, and retroviral vectors.

* * * * *